US010220363B2

United States Patent
de Lasa

(10) Patent No.: US 10,220,363 B2
(45) Date of Patent: Mar. 5, 2019

(54) REACTOR AND MULTIFUNCTIONAL RISER AND DOWNER SIMULATOR INCORPORATING THE SAME

(71) Applicant: THE UNIVERSITY OF WESTERN ONTARIO, London (CA)

(72) Inventor: Hugo de Lasa, London (CA)

(73) Assignee: The University of Western Ontario, London, Ontario (CA)

( * ) Notice: Subject to any disclaimer, the term of this patent is extended or adjusted under 35 U.S.C. 154(b) by 0 days.

(21) Appl. No.: 15/585,780

(22) Filed: May 3, 2017

(65) Prior Publication Data
US 2017/0320036 A1 Nov. 9, 2017

Related U.S. Application Data

(60) Provisional application No. 62/331,007, filed on May 3, 2016.

(51) Int. Cl.
| | | |
|---|---|---|
| *B01J 8/18* | (2006.01) | |
| *B01J 8/38* | (2006.01) | |
| *G01N 31/10* | (2006.01) | |

(52) U.S. Cl.
CPC ........... *B01J 8/1836* (2013.01); *B01J 8/1827* (2013.01); *B01J 8/382* (2013.01); *B01J 8/386* (2013.01);
(Continued)

(58) Field of Classification Search
CPC .................................. B01J 8/18; B01J 8/1836
(Continued)

(56) References Cited

U.S. PATENT DOCUMENTS

| | | | | | |
|---|---|---|---|---|---|
| 2,386,419 A | * | 10/1945 | Auer | ......................... | B01F 5/10 |
| | | | | | 210/196 |
| 5,102,628 A | * | 4/1992 | De Lasa | .................... | B01J 8/24 |
| | | | | | 422/139 |

FOREIGN PATENT DOCUMENTS

EP 0282777 A2 * 9/1988 ............ B01J 8/1818

OTHER PUBLICATIONS

I. Ahmed, S. Rostom, A. Lanza, and H. de Lasa—"Computational Fluid Dynamics study of the CREC Riser Simulator: Mixing patterns", Powder Technology 316 (2017) 641-649—Available online Dec. 7, 2016 (Year: 2016).*

(Continued)

*Primary Examiner* — Huy Tram Nguyen
(74) *Attorney, Agent, or Firm* — Michael Best & Friedrich LLP

(57) ABSTRACT

A reactor comprises a reactor vessel defining a confined reactor volume, a support assembly extending about a periphery of the confined reactor volume, a basket positioned within the reactor vessel and supported by the support assembly, the basket having an interior surface and an exterior surface, a downflow zone being defined between the exterior surface of the basket and an interior surface of the confined reactor volume, an inlet screen positioned adjacent to one end of the interior surface and an outlet screen positioned adjacent to an opposite end of the interior surface, an upflow zone defined between the inlet screen and outlet screen, the inlet screen and the outlet screen containing a quantity of particulate catalyst, and a circulating device positioned above said upflow zone and configured to continuously circulate fluid upwardly though said upflow zone and downwardly through said downflow zone, the support assembly and the basket configured to promote the formation of a fluid vortex within a portion of the downflow zone.

16 Claims, 9 Drawing Sheets

(52) U.S. Cl.
CPC .... *B01J 8/1854* (2013.01); *B01J 2208/00212* (2013.01); *B01J 2208/00884* (2013.01); *B01J 2208/00893* (2013.01); *B01J 2208/00964* (2013.01); *B01J 2219/00011* (2013.01); *G01N 31/10* (2013.01)

(58) Field of Classification Search
USPC ........................................................ 422/130
See application file for complete search history.

(56) References Cited

OTHER PUBLICATIONS

Daniel W. Kraemer and Hugo I. de Lasa—"Catalytic Cracking of Hydrocarbons in a Riser Simulator"—Ind. Eng. Chem. Res. 1988, 27, 2002-2008 (Year: 1988).*

* cited by examiner

REACTOR AND MULTIFUNCTIONAL RISER AND DOWNER SIMULATOR INCORPORATING THE SAME

CROSS-REFERENCE TO RELATED APPLICATIONS

This application claims the benefit of U.S. Provisional Application No. 62/331,007 to de Lasa filed May 3, 2016, entitled "Reactor and Multifunctional Riser and Downer Simulator Incorporating the Same" the entire disclosure of which is incorporated herein by reference.

FIELD

This invention relates to a reactor and a multifunctional riser and downer simulator incorporating the same.

BACKGROUND

A number of laboratory scale testing units are available to determine the activity of selected catalysts and their effect on catalytic cracking of various feedstocks.

U.S. Pat. No. 4,419,328 to Walsh discloses an apparatus for investigating the performance of a catalyst used in a catalytic cracking process. The apparatus includes a single fluidized bed reactor charged with the catalyst to be investigated and a digital computer which controls the supply of hydrocarbon feed stock and regenerating air in successive and repeated catalytic cracking intervals and catalyst regeneration intervals.

U.S. Pat. No. 5,102,628 to de Lasa discloses an apparatus for testing performance of a catalyst in a gaseous phase catalytic reaction for a given reactant. The apparatus comprises a reactor receiving a predetermined quantity of fluid reactant discharging the reaction mixture, including reaction products, from the reactor after a predetermined residence time. The reactor comprises a confined reactor volume with an upflow zone and a downflow zone. A device circulates fluids upwardly through the upflow zone and downwardly through the downflow zone where particulate catalysts in the upflow zone are fluidized by the upward flow of the fluid. The circulating device is adapted to circulate the fluid about the reactor volume at a rate which provides at any moment during the residence time for the reactants an essentially uniform concentration of reactants throughout the reactor volume to simulate conditions in a catalytic riser reactor. The unit provides generally the same residence time for both the fluid and the catalyst.

de Lasa discloses baffles positioned within the downflow zone to reduce and disturb the flow of fluid therethrough. The baffles are also used to prevent the forming of a vortex within the downflow zone. de Lasa also requires high impeller speeds thereby compromising the mechanical stability of the apparatus.

It is therefore an object to provide a novel reactor and a multifunctional riser and downer simulator incorporating the same.

SUMMARY

Accordingly, in one aspect there is provided a reactor comprising a reactor vessel defining a confined reactor volume, a support assembly extending about a periphery of the confined reactor volume, a basket positioned within the reactor vessel and supported by the support assembly, the basket having an interior surface and an exterior surface, a downflow zone being defined between the exterior surface of the basket and an interior surface of the confined reactor volume, an inlet screen positioned adjacent to one end of the interior surface and an outlet screen positioned adjacent to an opposite end of the interior surface, an upflow zone defined between the inlet screen and outlet screen, the inlet screen and the outlet screen containing a quantity of particulate catalyst, a circulating device positioned above said upflow zone and configured to continuously circulate fluid upwardly though said upflow zone and downwardly through said downflow zone, the support assembly and the basket configured to promote the formation of a fluid vortex within a portion of the downflow zone.

In an embodiment, the support assembly and the basket are configured to define an inverse frustoconical shape therebetween for promoting formation of the fluid vortex within the portion of the downflow zone. The support assembly and the basket are configured such that a width of the downflow zone is greater at a location below the inverse frustoconical shape than at a location above the inverse frustoconical shape.

In an embodiment, the circulating device rotates at a speed to permit formation of a fluid vortex within the upflow zone and formation of the fluid vortex in the downflow zone.

According to another aspect there is provided a simulator comprising a reactor having an inlet and an outlet, the reactor comprising a reactor vessel defining a confined reactor volume, a support assembly extending about a periphery of the confined reactor volume, a basket positioned within the reactor vessel and supported by the support assembly, the basket having an interior surface and an exterior surface, a downflow zone being defined between the exterior surface of the basket and an interior surface of the confined reactor volume, an inlet screen positioned adjacent to one end of the interior surface and an outlet screen positioned adjacent to an opposite end of the interior surface, an upflow zone defined between the inlet screen and outlet screen, the inlet screen and the outlet screen containing a quantity of particulate catalyst, a circulating device positioned above said upflow zone and configured to continuously circulate fluid upwardly though said upflow zone and downwardly through said downflow zone, the support assembly and the basket configured to promote the formation of a fluid vortex within a portion of the downflow zone.

BRIEF DESCRIPTION OF THE DRAWINGS

Preferred embodiments of the invention are shown in the drawings, wherein.

DETAILED DESCRIPTION OF THE PREFERRED EMBODIMENTS

The test unit, according to a preferred aspect of the invention, will be exemplified with respect to testing performance of catalysts in cracking reactions conducted in catalytic riser reactors.

Figure 1:
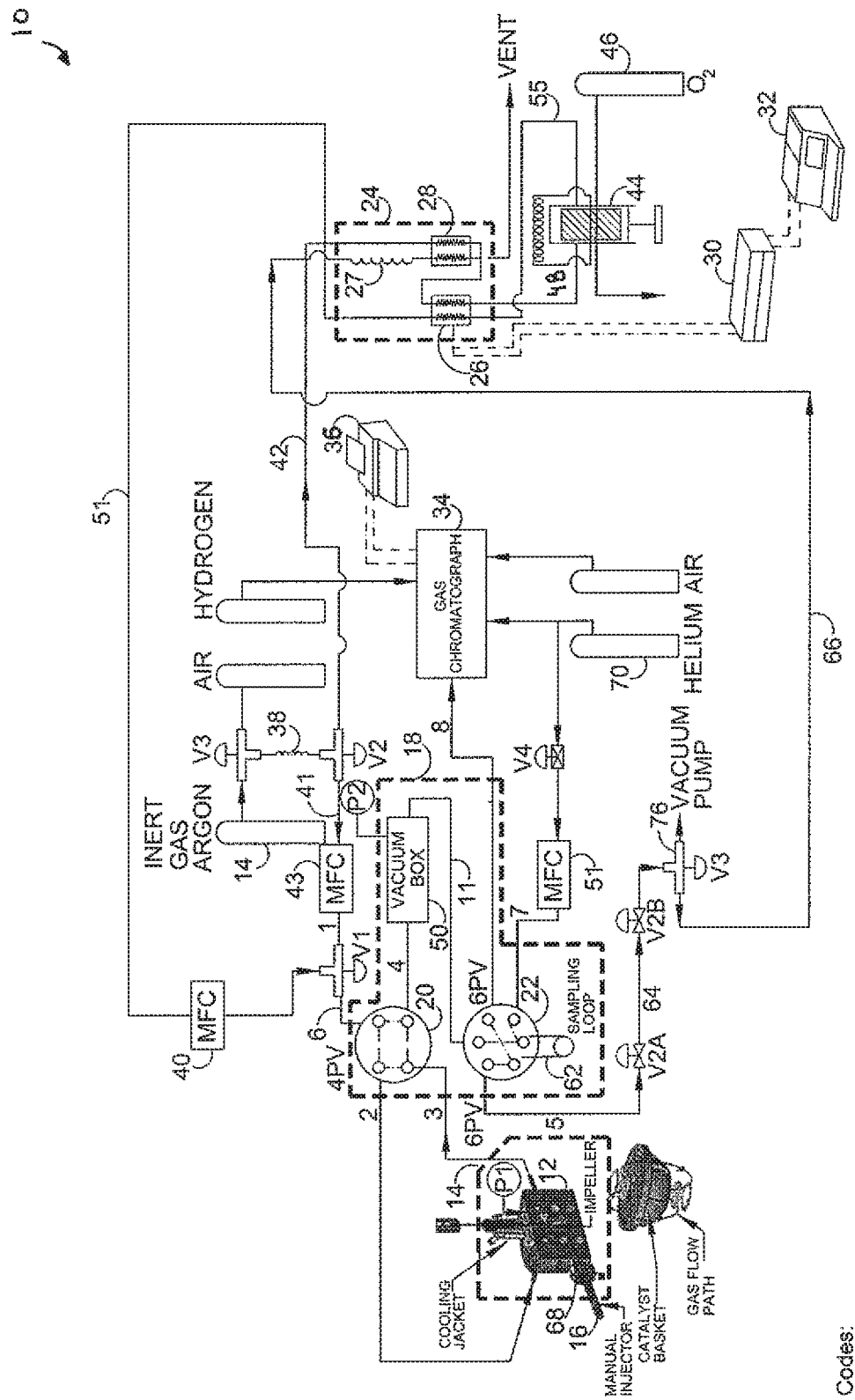
FIG. 1 is a schematic view of a testing unit.

With reference to FIG. 1, a schematic of an exemplary test unit is shown and is generally identified by reference numeral 10. In this embodiment, the test unit is in the form of a multifunctional riser and downer simulator. The test unit comprises a reactor 12. A carrier gas in the form of helium or argon supplied by cylinder 70. When the test unit is used to determine the effectiveness of the predetermined catalyst for a given feedstock, an injector system 16 is used to inject into the carrier gas a predetermined quantity of hydrocarbon feedstock material. An insulated heated enclosure or box 14 is provided which has a preset temperature. The box 14 and rod heaters 68 within the reactor 12 heat the reactor 12 at a predetermined temperature. All flows of fluids through the various conduits are controlled by two valves 20 and 22. Valve 20 (4 PV) controls the admission of fluids to the reactor 12, whereas valve 22 (6 PV) controls the withdrawal of fluids from the reactor 12. Presence of oxygen and catalyst regeneration products in incoming and outgoing streams are determined within thermal conductivity measuring system 24 having thermal conductivity measuring devices 26 and 28. The thermal conductivity, as indicated by electrical signals generated in sensors 26 and 28, are fed to an analog to digital converter 30 which in turn has an output to microprocessor 32 for recordal of relevant data. The reaction mixture, as withdrawn from the reactor 12 via vacuum box 50, is fed to a gas chromatograph 34 for analysis of the product composition. The output of the gas chromatograph is then fed to the integrator 36 for printout of the results.

In this embodiment, the testing unit 10 is set up to test hydrocarbon feedstock as would be injected by the injector system 16. In this embodiment, the weight of the catalyst is approximately 1 g and the temperature of the injector system is set at approximately 150° C. Two reactor sections of the reactor 12 are closed and tightened using nuts and bolts (not shown). In this embodiment, the temperature of the reactor 12 is increased to between 500° C. and 660° C. under inert gas flow. As will be appreciated, the temperature of the reactor 12 is maintained constant for the entire test run.

The thermal conductivity detectors 26 and 28 are brought to a set temperature with the help the heating coils of enclosure 24, while valves 20 and 22 are heated to approximately 300° C. The temperature of the reactor 12 is set and controlled at the level chosen for the test run. Heating tapes or the like may be used to heat the various conduits of the system while adequate sensors are employed to monitor the temperature in the lines. The temperature selected for the lines may be in the range of 300° C. to 400° C.

The inert carrier gas from tank 14 flows through filter 38 and line 42 to mass flow controller 40. As will be appreciated, the inert carrier gas may alternatively flow through line 41 through mass flow controller 43 and line 1. The helium flows through line 42 which passes through the non-sensing side of the thermal conductivity detector 28 and also through the non-sensing side of the thermal conductivity detector 26 before flowing through to the valve 44. The valve 44 is also connected to an oxygen supply tank 46 which supplies oxygen in the catalyst regeneration cycle.

The inert carrier gas continues to flow via line 55 which passes through the sensing side of thermal conductivity detector 26 and into valve 20 via lines 51 and 6. For the first position of the valve 20, line 6 is connected to line 2 to deliver the inert gas into the reactor 12 via an inlet. The inert carrier gas emerges through outlet line 3 into line 4 which is connected to vacuum box 50, line 11 to valve 22. For the first position of valve 22, line 11 is connected to line 5 via the sampling loop. As such, the first position of the valve 22 is the sample loading position. For the first position of both valves 20 and 22, line 5 delivers the gas via line 66 through the sensing side of thermal conductivity detector 28. Alternatively, if valve 22 is in the second position, line 6 connects with line 8 via the sampling loop and as such a sample is directed to the gas chromatograph 34.

In this embodiment, contact temperatures are maintained by heated boxes 14, 18, 24 and rod heaters 68. Heated box 18 is used to maintain the vacuum box 50, including the reaction products contained therein, at a set temperature and vacuum pressure. Heated box 14 and rod heaters 68 are used to maintain the hydrocarbon sample at a predetermined temperature inside the reactor 12. Heated box 24 is used to maintain the injected amounts of oxygen and catalyst regeneration products ($O_2$, $CO_2$ and $H_2O$) at set conditions for TCD measurements.

Once all temperatures in the test system have reached steady state and the rod heaters 68 for the reactor are also at steady state, a sample feedstock of hydrocarbon may be injected into the carrier stream. At this point, adequate current for the thermal conductivity detector is selected. At the same time, the other components of the data acquisition system including a flame ionization detector (FID) of the chromatograph 34 and the microprocessor are in the ready condition. Valve 20 is set in the second position with line 6 and line 4 connected and the reactor 12 being isolated. A hydrocarbon pulse of approximately 0.15 g is injected into the reactor 12. The hydrocarbon pulse is immediately vaporized in the reactor 12.

In changing the position of valve 20 to the second position, this modifies the operation of the testing unit from the continuous mode to the discontinuous mode of operation for the reactor 12. The reactor 12 is then isolated from the remainder of the set up. The inert carrier gas continuously circulates through the thermal conductivity detectors 26 and 28 the injector system 16 and the gas chromatograph 34. This is achieved because the valve 20 in its second position provides for interconnection of line 6 and line 4. The inert carrier gas then circulates without interruption, thereby keeping the operation of the thermal conductivity detectors and the flame ionization detector of the gas chromatograph 34 under steady state operation, minimizing oscillations or changes in the output signals of these instruments.

With the hydrocarbon sample placed into the injection syringe in port 16, the sample is ready for injection into the reactor 12. Intense mixing occurs in the fluidized bed of the reactor 12 where all catalyst particles are essentially surrounded by a hydrocarbon mixture of the same composition at any given time. The manner in which this is accomplished will be discussed with respect to the particular views of the reactor structure. A predetermined residence time for the hydrocarbon mixture is provided. When that time is expired, valve 20 is moved to a first position to connect line 6 with line 2 and line 3 with line 4.

Rapid withdrawal of the reaction from the reactor 12 is accomplished by use of vacuum box 50 which is controlled by valve 20 as connected to line 4 and to line 11. Valves 76, V2A and V2B are opened to apply vacuum to the lines 4, 11 and 5 and to the vacuum box 50. The valves are then shut off. The vacuum box 50 is heated via heated box 18, operating a temperature in the range of 300° C. to 350° C. Once the temperature has been reached, the pressure inside the vacuum box is reduced to a range of 0.5 psi and 1.5 psi using a vacuum pump (not shown). By moving the valve 20 to the second position, vacuum is established in the lines 4, 5 and 11 and the vacuum 50. As such, the contents of the reactor 12 can be immediately withdrawn with the reaction mixture moving through line 4 into the vacuum box 50. Due to the speed at which the reaction mixture is withdrawn from the reactor, further transformation of the products evacuated from the reactor are quickly and effectively stopped. In addition, the controlled temperature in the heated box 18 is sufficiently low in the range of 300° C. to 350° C. to stop further reaction without risking condensing of products in the vacuum box 50.

Now that the reaction mixture has been removed and no further reaction can continue, it is necessary to deliver the reaction mixture from the vacuum box 50 to the gas chromatograph 34. The hydrocarbon sample is now located vacuum box 50. With the valve 22 in the second position with lines 5 and 6 interconnected for the second position of valve 20, the sample moves through the sampling loop 62, line 5 and line 64 once valve V2A is open.

By switching valve 20 back to its first position with line 6 connected to line 2 and line 3 connected to line 4, the continuous flow of inert helium is re-established through the reactor 12. The hydrocarbon product sample, as located in the sampling loop, circulates through the lines 11 and 8 as reconnected at the first position for valve 22, through connected line 11 and line 8 and into the flame ionization detector of the gas chromatograph 34. The gas chromatograph analysis is conducted using a liquid nitrogen-cryogenic option in order to have the different reaction products in a single chromatogram as specifically adapted to analyze the products of the catalytic reaction.

As will be appreciated, the testing apparatus 10 provides a continuous flow of inert carrier gas through the system to provide for a steady state condition and then to inject a sample of reactant into the reactor via the carrier gas. At that instance, flow of the carrier gas is interrupted to provide for discontinuous operation of the system. While the reactants are in the reactor, the system is monitored to provide for a predetermined residence time at which point the reaction mixture is rapidly withdrawn from the reactor. As noted, the system is used to simulate reaction conditions in a conventional catalytic riser reactor. The system may also be used to simulate the conditions in regeneration of spent catalyst. As will be described, the reactor 12 is specially designed to provide at any instance during the residence time of the reactants in the reactor an essentially constant concentration of reactants in any portion of the reactor volume.

As mentioned previously, the test unit 10 may be used to test regeneration of catalysts by introducing oxygen via the feeding valve 44 to regenerate catalyst contained in the reactor 12. Once the oxygen pulse size and shape are determined by the thermal conductivity detector 26, the oxygen sample continues circulating via line 55, line 51 and line 6, reaching valve 20. At this point, the valve 20 is switched to the first position such that lines 1 and 2 are connected and lines 3 and 4 are connected.

The valve 44 is used to inject a predetermined quantity of oxygen into the inert gas carrier line. With the valves 20 and 22 in the first position, valve 44 is pushed to a load position and a pulse of oxygen is introduced into line 48. After contacting the catalyst for a preset time, which in this embodiment is between 2 seconds and 20 seconds after the oxygen is introduced into the reactor 12, the products of combustion ($O_2$, CO, $CO_2$ and $H_2O$) are carried from the reactor 12 via lines 3, 4, 11, 5, 64, and 66. In this embodiment, the products of the coke combustion are analyzed using a CARBOWAX™ (a trademark of Union Carbide for a polyethylene glycol material) column 27 and a detecting side of the thermal conducting detector 28. As will be appreciated, this type of column provides an adequate separation for the combustion products to evaluate the effectiveness of the regeneration process in regenerating the catalyst.

Figure 2:
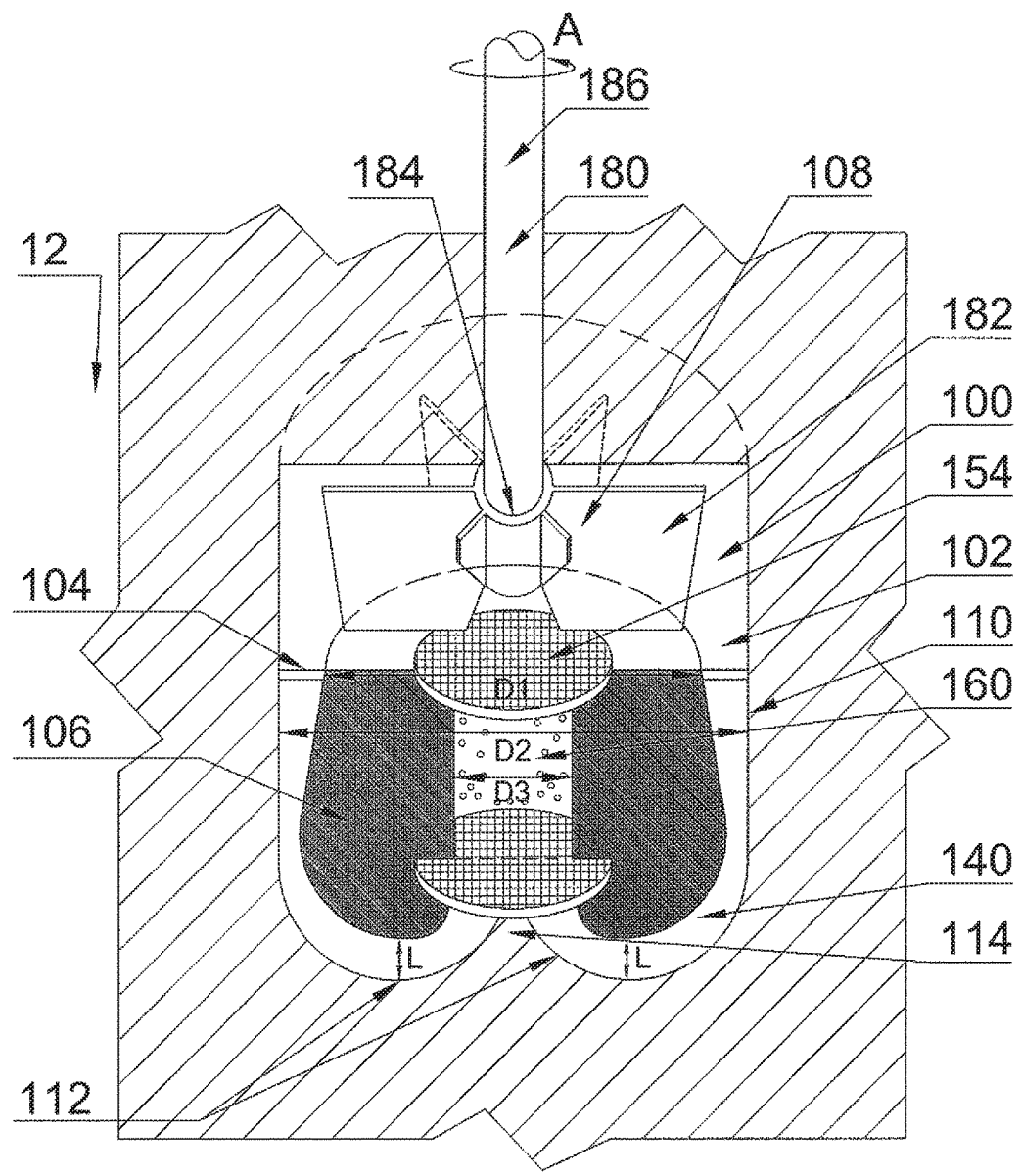
FIG. 2 is a cross-sectional view of a reactor forming part of the test unit of FIG. 1.

Turning now to FIG. 2, a perspective view of the reactor 12 is shown. As can be seen, the reactor 12 comprises a reactor vessel 100 defining a confined reactor volume 102. A support assembly 104 extends about a periphery of the confined reactor volume 102. A basket 106 is positioned within the confined reactor volume 102 and is supported by the support assembly 104. A circulating device 108 is positioned above the basket 106 and is configured to circulate fluid throughout the confined reactor volume 102.

The confined reactor volume 102 has an interior surface 110 comprising a generally rounded bottom surface 112. A peak 114 extends upward at an approximate midpoint of the rounded bottom surface 112.

Figure 3:
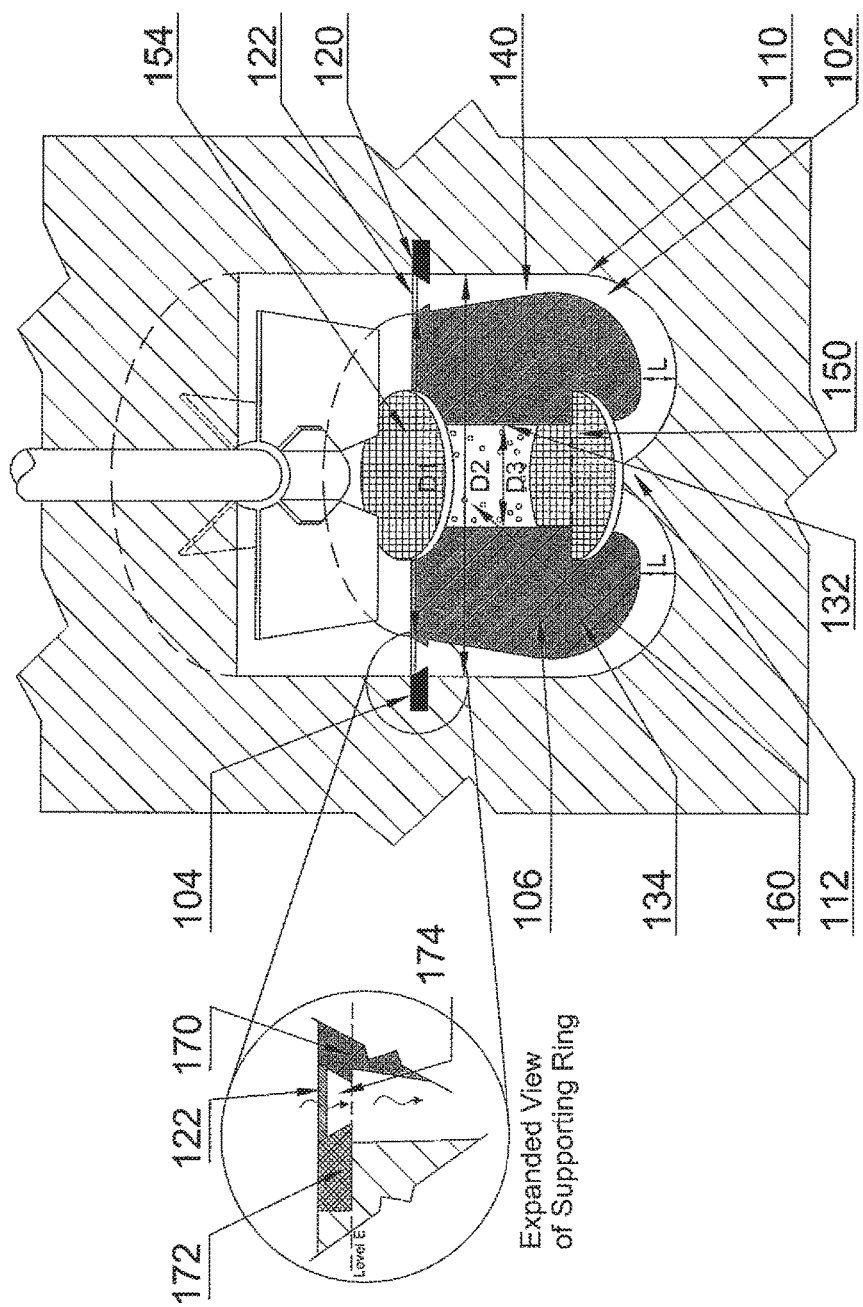
FIG. 3 is an expanded view showing part of the reactor of FIG. 2.

FIG. 3 is an expanded view of the reactor 12 better showing the support assembly 104 and the basket 106. The support assembly 104 comprises a support ring 120 extending about the periphery of the confined reactor volume 102. A plurality of pins 122, in this embodiment three (3), are generally evenly spaced about the support ring 120 and extend radially inward therefrom. The pins 122 are in contact with and support the basket 106 within the confined reactor volume 102.

The basket 106 is generally annular. The basket 106 is made of a non-reactive material such as for example high grade stainless steel. The basket 106 has an interior surface 132 extending generally vertically therethrough and an exterior surface 134. The basket 106 is positioned within the confined reactor volume 102 such that the peak 112 extends towards the interior surface 132, reaching a lower face of a porous screen 137.

A downflow zone 140 is defined between the exterior surface 134 of the basket 106 and the interior surface 110 of the confined reactor volume 102.

An inlet screen 150 is positioned adjacent to one end of the interior surface 132 of the basket 106. An outlet screen 154 is positioned adjacent to an opposite end of the interior surface 132 of the basket 106. An upflow zone 160 is defined between the inlet screen 150 and the outlet screen 154. In this embodiment, the inlet screen 150 and the outlet screen 154 are removable to permit replacement of a catalyst contained within the upflow zone 160. As will be appreciated, the inlet screen 150 and the outlet screen 154 are also removable for periodic replacement thereof.

A top portion 170 of the basket 106 and an inner edge 172 of the support ring 120 are shaped to together define an inverse frustoconical shaped section 174 therebetween. The top portion 170 of the basket 106 and the inner edge 172 of the support ring 120 are also shaped such that the width of the downflow zone 140 is greater below the inverse frustoconical shaped section 174 than the width of the downflow zone 140 above the inverse frustoconical shaped section 174. As such, any fluid flowing through the downflow zone 140 will accelerate through the inverse frustoconical shaped section 174, thereby minimizing the effect of the pins 122.

Turning back to FIG. 2, the circulating device 108 is positioned above the upflow zone 160 and is configured to continuously circulate fluid upwardly though said upflow zone 160 and downwardly through said downflow zone 140. In this embodiment, the circulating device 108 is in the form of a rotating impeller 180. The impeller 180 is positioned directly above the outlet screen 154. The impeller 180 comprises a plurality of vanes 182 attached to a hub 184 of a drive shaft 186. The impeller 180 is rotated by the drive shaft 186 in the direction of arrow A. The impeller 180 is configured to rotate at a sufficient speed to cause the fluids to flow through the upflow zone 160 to fluidize the bed of catalysts contained therein.

During operation, the impeller 180 rotates in the direction indicated by arrow A at a speed of approximately 2000 rpm to 5500 rpm. As such, fluid within the reactor 12 is caused to move in a direction indicated by arrows C. Specifically, fluid travels down the downflow zone 140. The inverse frustoconical shape 174 formed by the top portion 170 of the basket 106 and an inner edge 172 of the support ring 120 causes fluid to form a first vortex. The rounded bottom surface 112 and peak 114 direct fluid through the inlet screen 150 and into the upflow zone 160. Due to the speed at which the impeller 180 rotates, a second vortex forms within the upflow zone 160. The fluid mixes with catalyst contained between the inlet screen 150 and outlet screen 154 thereby causing particle fluidization. The fluid and catalyst continues to travel though the upflow zone 160 and out through the outlet screen 154, where fluid separated from the catalyst is directed towards the downflow zone 140.

Figure 4:
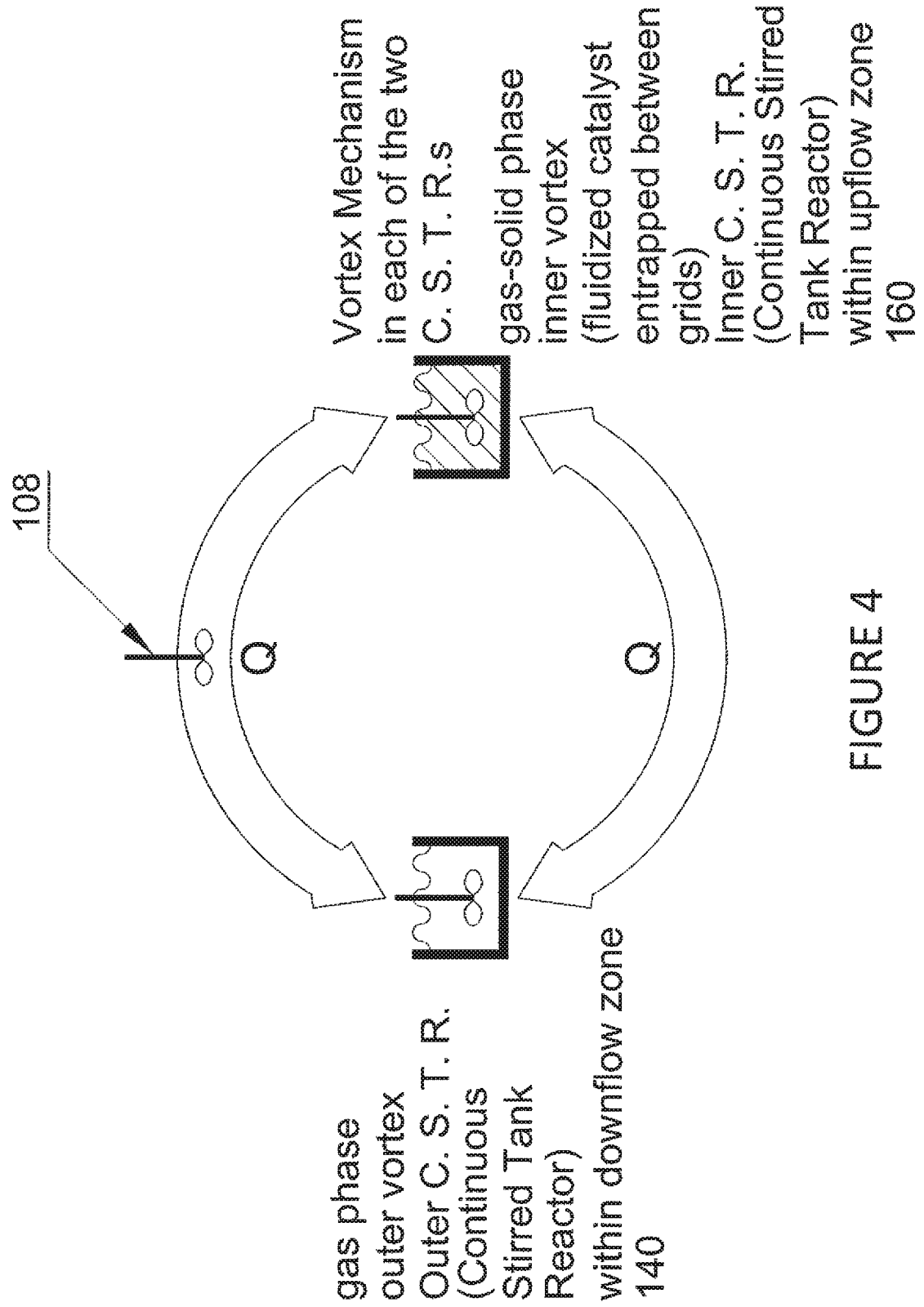
FIG. 4 is a block diagram showing two vortices formed by the reactor of FIG. 2.

The formation of first and second vortices provides two continuous stirred tank reactors operating in a closed loop as shown in FIG. 4. The first vortex forms during the gas-phase in the downflow zone 140. The second vortex forms during the gas-solid phase in the upflow zone 160.

Thus, particle fluidization occurs in the upflow zone 160 and a mixing during the gas phase occurs in the downflow zone 140. The mass balance representing chemical changes as a result of the catalyst is calculated according to equation 1:

$$V_{reactor} dC_A/dt = (-r_c) W_c \quad (1)$$

where $V_{reactor}$ is the reactor volume, $C_A$ is the concentration of the reactor inside the unit, t is the reaction time, $r_c$ is the catalytic rate of reaction of function of $C_A$, and $W_c$ is the weight of the fluidizable catalyst. As will be appreciated, equation 1 requires a single concentration value at in the entire reactor volume at a given residence. This is the case, given $r_c$ being a function of $C_a$, has to display a single $r_c$ rate value for the entire $W_c$ catalyst mass of catalyst at a t time. This is accomplished due to the formation of the first and second vortices which causes intense gas mixing in both the upflow zone 160 and the downflow zone 140. As will be appreciated, the reactor 12 may be used for catalyst testing and for accurate reaction modeling using equation (1).

Figure 6:
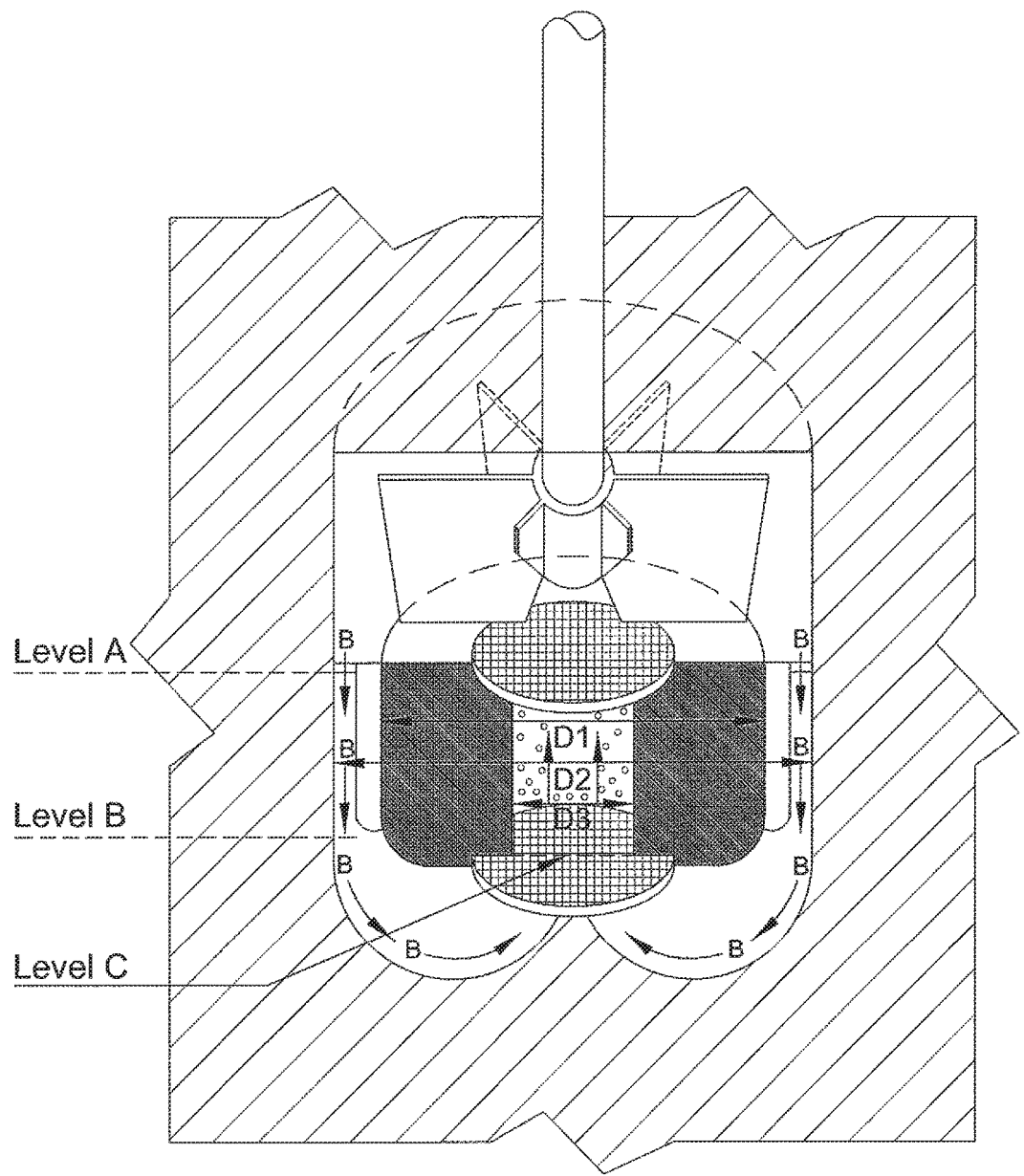
FIG. 6 is a cross-sectional view of a prior art rector identifying various levels therein.

In comparison with prior art reactors, reactor 12 provides an increased flow of gas. For example, FIG. 6 shows a prior art reactor such as that described in U.S. Pat. No. 5,102,628 to de Lasa et al. The flow of the fluid within the reactor is indicated by arrows B. Table 1 shows the area and velocity at various levels within the reactor:

TABLE 1 for Volumetric Flow of 513 cm³/s in Prior Art Reactor

| Level | Area (cm²) | U (m/s) |
|---|---|---|
| Level A (annular flow area, $D_{annulus, in}$ = 3.67 cm, $D_{annulus, out}$ = 4.35 cm) | 4.28 | 1.2 |
| Level B (annular flow $D_{annulus, in}$ = 3.67 cm, $D_{annulus, out}$ = 4.35 cm) | 4.28 | 1.2 |
| Level D (cylindrical flow area with D = 3 cm, L = 1 cm) | 9.42 | 0.54 |
| Level C (circular flow area with D = 1.6 cm) | 1.256 | 4.09 |

Figure 5:
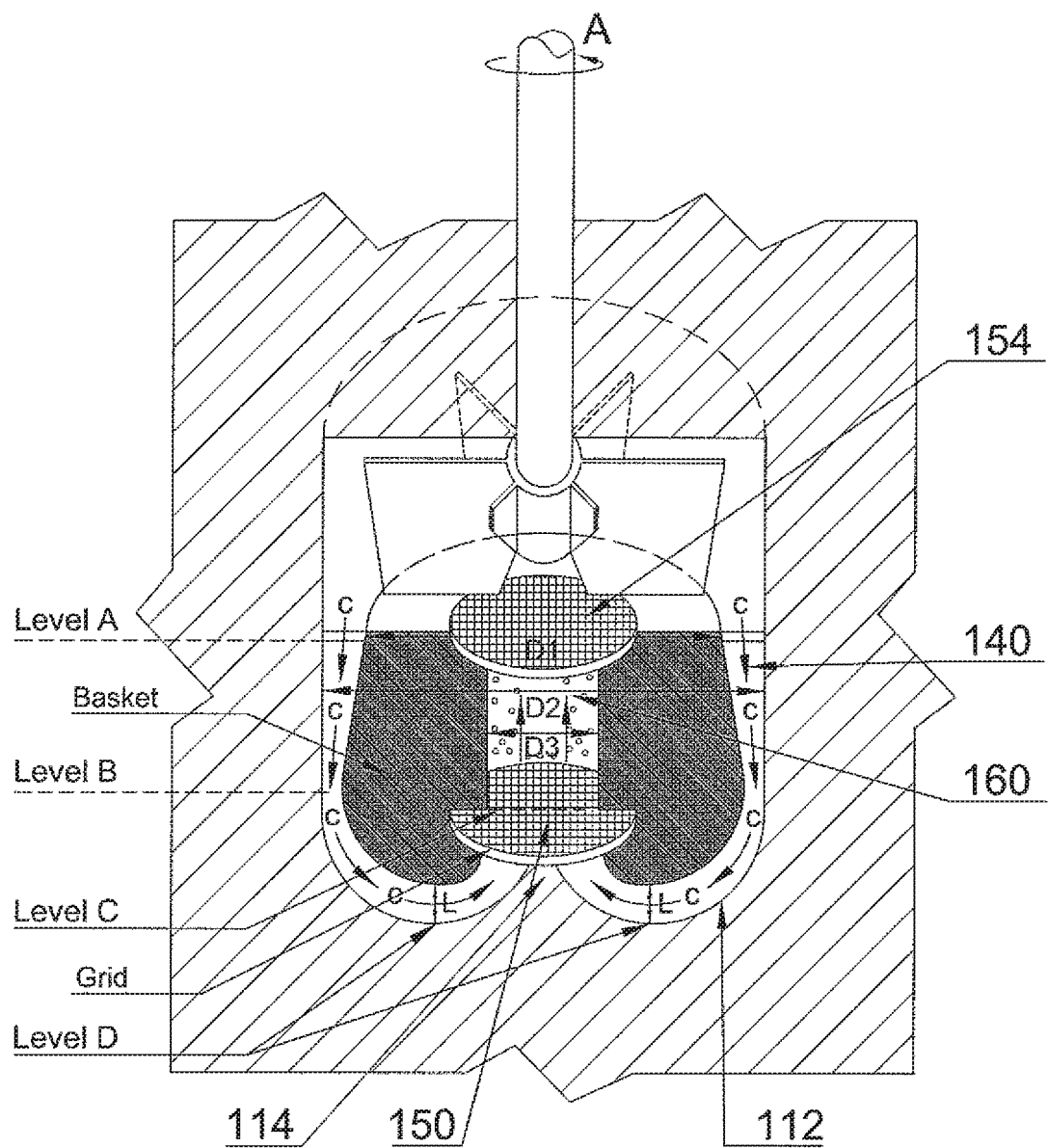
FIG. 5 is a cross-sectional view of the reactor of FIG. 2 identifying various levels therein.

Table 2 shows the area and velocity at various levels within the reactor 12 (see FIG. 5):

TABLE 2 for Volumetric Flow of 513 cm³/s of Reactor 12

| Level | Area (cm²) | U (m/s) |
|---|---|---|
| Level A (annular flow area, $D_{annulus, in}$ = 3.67 cm, $D_{annulus, out}$ = 4.35 cm) | 4.28 | 1.2 |
| Level B (annular flow $D_{annulus, in}$ = 3.9 cm, $D_{annulus, out}$ = 4.35 cm) | 2.91 | 1.76 |
| Level D (cylindrical flow area with D = 3 cm, L = 0.2 cm) | 1.84 | 2.73 |
| Level C (circular flow area with D = 1.6 cm) | 1.256 | 4.09 |

Comparing the velocity for Levels A, B, D and C in Tables 1 and 2 shows that the velocity has increased in Levels B and D for reactor 12 (compared to the prior art reactor).

Figure 7:
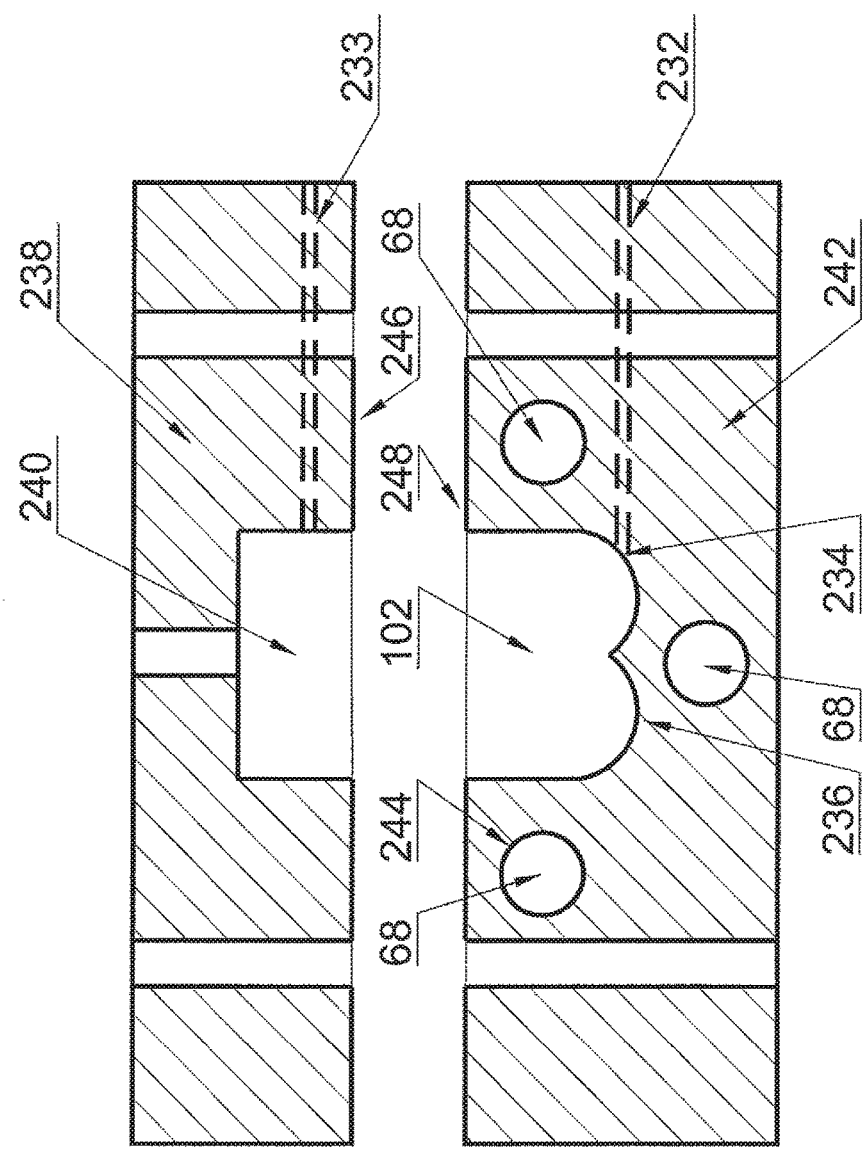
FIG. 7 is an exploded vertical cross-section through the reactor of FIG. 2 showing the sealing and cooling jacket.
Figure 8:
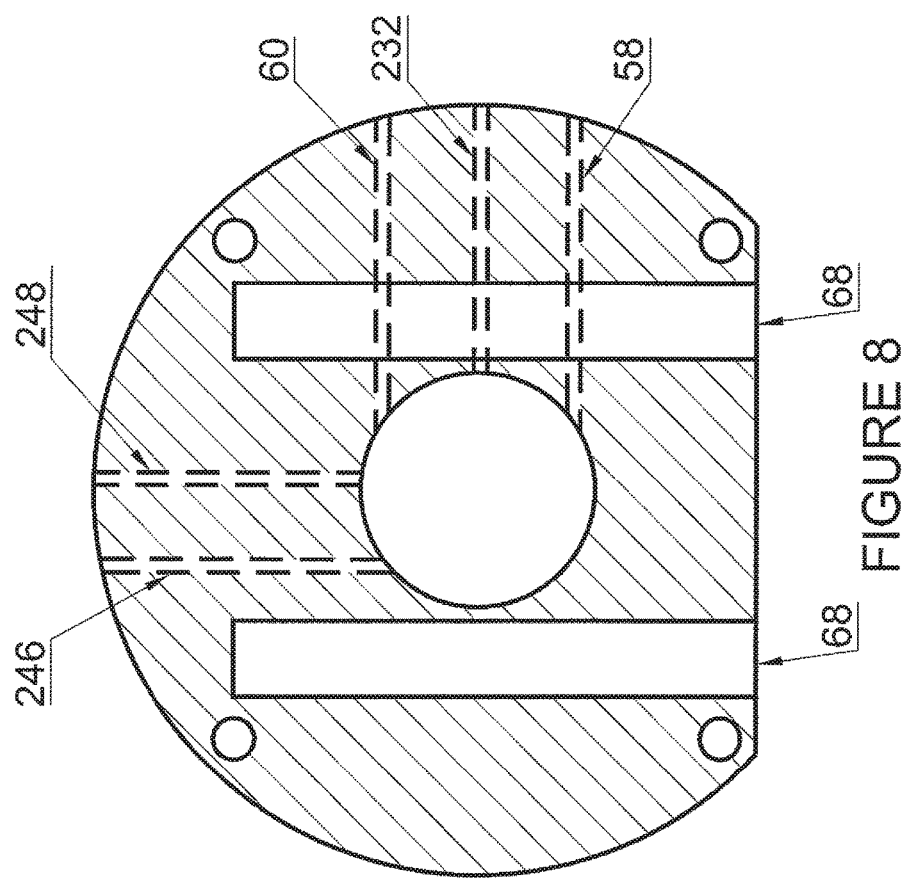
FIG. 8 is a top view of a section of the reactor of FIG. 2.

To monitor both the temperature inside the reactor 12 as well as the quality of the fluidized bed in the upflow zone 160, two pressure taps are employed as shown in FIGS. 7 and 8. Minute bores 232 and 233 extend into a lower region 234 and into an upper region 240 of the confined reactor volume 102. By monitoring the pressure at these points in the reactor, it is possible to determine the consistency of a fluidized bed throughout the run of the testing device.

Figure 9:
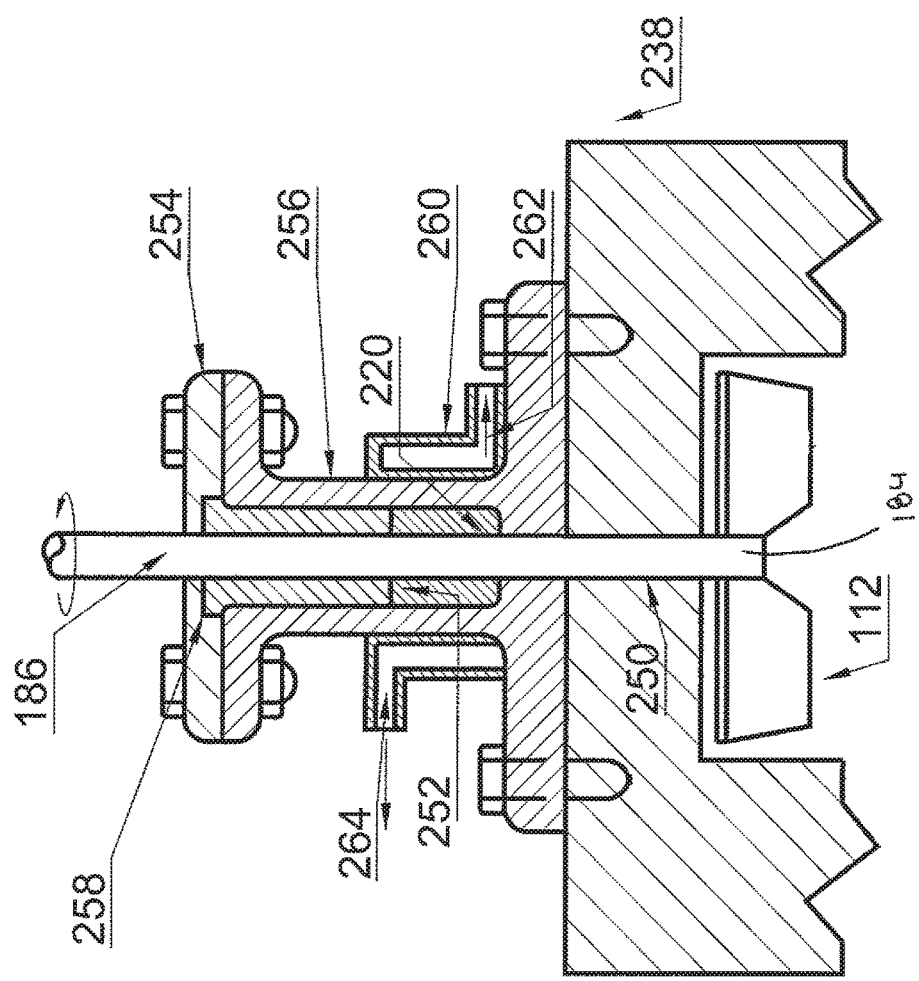
FIG. 9 is a bottom view of the reactor of FIG. 2 showing two injection ports.

The inlet 58 for the reactor is shown in FIGS. 7 and 8. The inlet 58 extends through an lower block portion 248 of the reactor 12 into the lower region 240 of the confined reactor volume 102. The outlet 60 for the reactor 12 also extends through the upper block portion 238 and communicates with the upper portion 240 of the confined reactor volume 102. Hence the reactants are introduced at the lower reactor 12 section and extracted at the tip portions of the impeller blade 182 (as shown in FIG. 9).

The lower block portion 242 of the reactor 12 carries the heater units 68 in the bores 244. A controller (not shown) is used to heat the reactor 12 to the desired temperature and maintain it at that temperature. In providing such control, thermocouples are located in bores 232 and 233 to monitor the temperature at all times in the system. When it is desired, the reactor 12 is assembled by clamping the block portions 238 and 242 together by use of suitable mechanical fasteners, clamps or the like. The interfaces 246 and 248 are machined so as to provide a suitable seal for the confined reactor volume 102.

It is important to provide a suitable seal at the interface of the impeller shaft 186 and the upper block portion 238. As shown in FIG. 9, the shaft 186 extends through bore 250 and is sealed in the region of 220a by a packing 252. The packing is compressed by way of cap 254 bolted to the packing retainer 256. A sleeve 258 compresses the packing 252 by bolting the flange 254 in place. Due to the high temperatures of the reactor, cooling about the packing retaining body is required to prevent heat from the reactor degrading the packing. A cooling jacket 260 is provided through which cooling water is circulated by inlet 262 and outlet 264. In addition, the cooling ensures that the packing does not overheat during high speed rotations of the shaft 186. In this manner, the confined reactor volume 102 is sealed in the region of the impeller as it extends through the reactor block 238.

With this design for the reactor, the conditions of catalytic riser and catalytic downer reactors can be simulated. By suitable operation of the valves 20 and 22 in the manner previously discussed which may be either manually or computer controlled, the switching from continuous flows through the reactor to a discontinuous residence time of reactants in the reactor is readily achieved. This set up therefore allows the monitoring of the amount of hydrocarbon feedstock injected, the quality of the mixing in the reactor vessel, the adequacy of the hydrocarbon injection and the effectiveness of the product evacuation from the reactor by the vacuum withdrawal system.

The scope of the claims should not be limited by the preferred embodiments set forth in the examples, but should be given the broadest interpretation consistent with the description as a whole.

What is claimed is:

1. A reactor comprising:
   a reactor vessel defining a confined reactor volume;
   a support assembly extending about a periphery of the confined reactor volume;
   a basket positioned within the reactor vessel and supported by the support assembly, the basket having an interior surface and an exterior surface, a downflow zone being defined between the exterior surface of the basket and an interior surface of the confined reactor volume;
   an inlet screen positioned adjacent to one end of the interior surface and an outlet screen positioned adjacent to an opposite end of the interior surface, an upflow zone defined between the inlet screen and outlet screen, the inlet screen and the outlet screen containing a quantity of particulate catalyst; and
   a circulating device positioned above said upflow zone and configured to continuously circulate fluid upwardly though said upflow zone and downwardly through said downflow zone;
   the support assembly and the basket configured to promote the formation of a fluid vortex within a portion of the downflow zone,
   wherein the support assembly and the basket are configured to define an inverse frustoconical shape therebetween for promoting formation of the fluid vortex within the portion of the downflow zone.

2. The reactor of claim 1 wherein the support assembly comprises a support ring extending about the periphery of the confined reactor volume.

3. The reactor of claim 2 wherein the support assembly comprises at least two pins extending radially inward from the support ring, the at least two pins supporting the basket.

4. The reactor of claim 1 wherein the circulating device is an impeller.

5. The reactor of claim 1 wherein the support assembly and the basket are configured such that a width of the downflow zone is greater at a location below the inverse frustoconical shape than at a location above the inverse frustoconical shape.

6. The reactor of claim 1 wherein the basket is generally annular shaped and comprises an oblong body.

7. The reactor of claim 1 wherein a bottom surface of the confined reactor volume comprises a peak extending generally upwards towards the interior surface of the basket.

8. The reactor of claim 1 wherein at least one of the inlet and outlet screens are removable to permit replacement of a catalyst contained therein.

9. The reactor of claim 1 wherein the circulating device rotates at a speed between 1000 rpm and 7000 rpm.

10. The reactor of claim 1 wherein the circulating device rotates at a speed to permit formation of a fluid vortex within the upflow zone and formation of the fluid vortex in the downflow zone.

11. A simulator comprising:
    a reactor having an inlet and an outlet, the reactor comprising:
      a reactor vessel defining a confined reactor volume;
      a support assembly extending about a periphery of the confined reactor volume;
      a basket positioned within the reactor vessel and supported by the support assembly, the basket having an interior surface and an exterior surface, a downflow zone being defined between the exterior surface of the basket and an interior surface of the confined reactor volume;
      an inlet screen positioned adjacent to one end of the interior surface and an outlet screen positioned adjacent to an opposite end of the interior surface, an upflow zone defined between the inlet screen and outlet screen, the inlet screen and the outlet screen containing a quantity of particulate catalyst; and
      a circulating device positioned above said upflow zone and configured to continuously circulate fluid upwardly though said upflow zone and downwardly through said downflow zone;
      the support assembly and the basket configured to promote the formation of a fluid vortex within a portion of the downflow zone,
      wherein the support assembly and the basket are configured to define an inverse frustoconical shape therebetween for promoting formation of the fluid vortex within the portion of the downflow zone.

12. The simulator of claim 11 further comprising:
    a heat box configured to heat the reactor to a predefined temperature.

13. The simulator of claim 11 further comprising:
    an injection system configured to inject a hydrocarbon sample into the upflow zone of the reactor.

14. The simulator of claim 13 further comprising:
    a vacuum configured to withdraw fluid containing chemical product species from the reactor via an outlet.

15. The simulator of claim 11 further comprising:
    an inlet configured to selectively permit the ingress of a reactant into the reactor.

16. The simulator of claim 11 wherein the simulator is one of a riser simulator and a downer simulator.

* * * * *